United States Patent
Yanagi et al.

(10) Patent No.: US 9,522,110 B1
(45) Date of Patent: Dec. 20, 2016

(54) CERAMIDE DISPERSION COMPOSITION

(71) Applicant: FUJIFILM CORPORATION, Minato-ku, Tokyo (JP)

(72) Inventors: Terukazu Yanagi, Kanagawa (JP); Hiroyuki Kitaoka, Kanagawa (JP); Akina Nakaune, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/224,671

(22) Filed: Aug. 1, 2016

(30) Foreign Application Priority Data

Sep. 25, 2015 (JP) ................. 2015-188409

(51) Int. Cl.
*A61K 8/63* (2006.01)
*A61Q 17/00* (2006.01)
*A61K 8/68* (2006.01)
*A61K 8/55* (2006.01)

(52) U.S. Cl.
CPC .............. *A61K 8/68* (2013.01); *A61K 8/553* (2013.01); *A61K 8/63* (2013.01); *A61Q 17/00* (2013.01); *A61K 2800/40* (2013.01); *A61K 2800/596* (2013.01)

(58) Field of Classification Search
CPC ............ A61K 8/68; A61K 8/553; A61K 8/63; A61Q 17/00
USPC ....................................................... 514/171
See application file for complete search history.

(56) References Cited

U.S. PATENT DOCUMENTS

2011/0076311 A1* 3/2011 Serizawa ............. A23L 33/12
424/401

FOREIGN PATENT DOCUMENTS

WO 2015/136784 A1 9/2015

OTHER PUBLICATIONS

WO2015136784 machine translation.*

* cited by examiner

*Primary Examiner* — Yevegeny Valenrod
(74) *Attorney, Agent, or Firm* — SOLARIS Intellectual Property Group, PLLC

(57) ABSTRACT

A ceramide dispersion composition, includes: at least one ceramide represented by Formula (1) or Formula (2); a surfactant; and trisodium ascorbyl palmitate phosphate, wherein in Formula (1), $R^1$ represents an aliphatic hydrocarbon group having at least one unsaturated double bond, $R^2$ represents an alkyl group having 9 or more carbon atoms, and n represents an integer from 20 to 34; and in Formula (2), $R^3$ represents an aliphatic hydrocarbon group having at least one unsaturated double bond, $R^4$ represents an alkyl group having 9 or more carbon atoms, m represents an integer from 20 to 34, and X represents a hydrogen atom or a hydroxyl group.

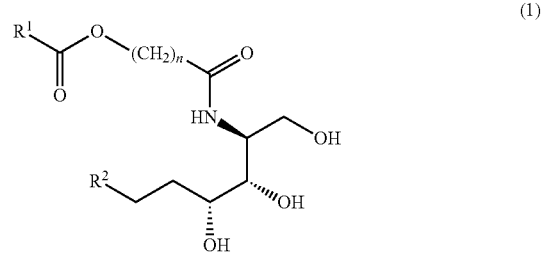

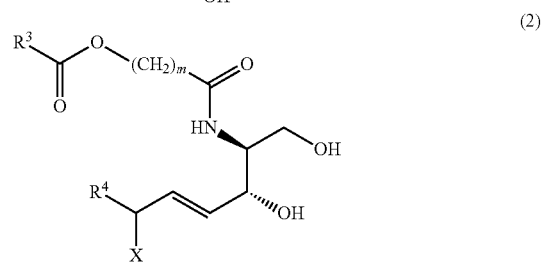

9 Claims, No Drawings

CERAMIDE DISPERSION COMPOSITION

CROSS-REFERENCE TO RELATED APPLICATION

This application claims priority under 35 USC 119 from Japanese Patent Application No. 2015-188409 filed on Sep. 25, 2015, the disclosure of which is incorporated by reference herein.

BACKGROUND OF THE INVENTION

Field of the Invention

The present invention relates to a ceramide dispersion composition.

Description of the Related Art

Ceramide is a major component of intercellular lipids in a horny cell layer existing among horny cells of skin. The intercellular lipids in a horny cell layer such as ceramide are layered to form a periodic structure (lamella structure) and fill the gaps among horny cells, thereby exhibiting the barrier function of skin.

In a lamella structure which is formed of intercellular lipids in a horny cell layer, there are two types of lamella structures, namely, a short periodic lamella structure (Short Periodicity Phase; hereinafter also referred to as "SPP") having a layer thickness of approximately 6 nm, and a long periodic lamella structure (Long Periodicity Phase, hereinafter also referred to as "LPP") having a layer thickness of approximately 13 nm. Especially, it is known that an LPP formed of a ceramide having an O-acyl moiety (also referred to as "acyl ceramide") as an essential component greatly contributes to the barrier function of skin.

The amount of ceramide in skin decreases owing to aging or the like, whereby the barrier function of skin decreases. In addition, in the case of the skin of a patient suffering from atopic dermatitis, it is known that the amount of ceramide decreases not only in a lesional part but also in a non-lesional part. Accordingly, in recent years, various kinds of ceramide dispersion compositions have been developed in expectation of a skin care effect or the like of ceramide.

In order to sufficiently cause an effect such as a skin care effect expected to be exhibited by ceramide, it is necessary to enhance the skin penetration of ceramide. Taking the skin penetration of ceramide into consideration, it is desired that the particle diameter of dispersed particles including ceramide is small. However, it is difficult to microsize dispersed particles including, especially, a ceramide having an O-acyl moiety, because the ceramide has a large molecular weight and a hydrophobic structure, and the ceramide is easy to crystallize. In addition, even after dispersing a ceramide having an O-acyl moiety, it is difficult to prevent aggregation or the like to keep the dispersion stability.

Under such a background, International Publication WO 2015/136784 discloses a ceramide-containing composition which contains a specific ceramide having an O-acyl moiety and a nonionic surfactant, in which the average particle diameter of dispersed particles is less than 60 nm. The ceramide-containing composition disclosed in International Publication WO 2015/136784 has small fluctuation of the particle diameter of dispersed particles even in a case in which the ceramide-containing composition has been stored, for example, at 50° C. for 90 days, so that the dispersion stability under a high temperature condition is excellent.

SUMMARY OF THE INVENTION

In a horny cell layer of skin, a large amount of ceramides having an unsaturated double bond in the O-acyl moiety are present. In recent years, these ceramides having an unsaturated double bond in the O-acyl moiety have been attracting attention because the ceramides stabilize a lamella structure in a horny cell layer.

However, ceramides having an unsaturated double bond in the O-acyl moiety may have poor oxidation stability. Accordingly, also in the case of a ceramide-containing composition in which the dispersion stability improves as in International Publication WO 2015/136784, further improvement of oxidation stability is desired.

The present disclosure has been made in view of circumstances such as those mentioned above. According to an aspect of the present invention, a ceramide dispersion composition is provided, which contains a ceramide having an unsaturated double bond in the O-acyl moiety and which is excellent in oxidation stability and dispersion stability.

The invention includes the following aspects.

<1> A ceramide dispersion composition, comprising:
at least one ceramide represented by Formula (1) or Formula (2);
a surfactant; and
trisodium ascorbyl palmitate phosphate:

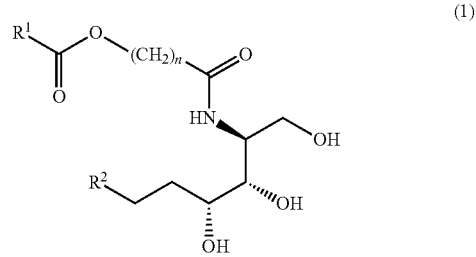

wherein, in Formula (1), $R^1$ represents an aliphatic hydrocarbon group having at least one unsaturated double bond, $R^2$ represents an alkyl group having 9 or more carbon atoms, and n represents an integer from 20 to 34; and

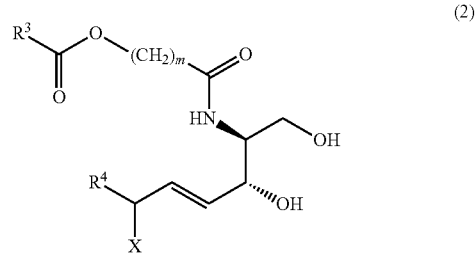

in Formula (2), $R^3$ represents an aliphatic hydrocarbon group having at least one unsaturated double bond, $R^4$ represents an alkyl group having 9 or more carbon atoms, m represents an integer from 20 to 34, and X represents a hydrogen atom or a hydroxyl group.

<2> The ceramide dispersion composition according to <1>, wherein the aliphatic hydrocarbon group having at least one unsaturated double bond represented by $R^1$ or $R^3$ has 15 or more carbon atoms.

<3> The ceramide dispersion composition according to <1> or <2>, wherein the aliphatic hydrocarbon group having at least one unsaturated double bond represented by $R^1$ or $R^3$ has from 1 to 3 double bonds.

<4> The ceramide dispersion composition according to any one of <1> to <3>, wherein the surfactant comprises a nonionic surfactant.
<5> The ceramide dispersion composition according to any one of <1> to <4>, further comprising lecithin.
<6> The ceramide dispersion composition according to any one of <1> to <5>, further comprising cholesterol.
<7> The ceramide dispersion composition according to any one of <1> to <6>, wherein a content of trisodium ascorbyl palmitate phosphate with respect to a content of the at least one ceramide represented by Formula (1) or Formula (2) is from 1 time by mass to 8 times by mass.
<8> The ceramide dispersion composition according to any one of <1> to <7>, wherein a content of the surfactant with respect to a content of the at least one ceramide represented by Formula (1) or (2) is from 1 time by mass to 70 times by mass.
<9> The ceramide dispersion composition according to any one of <1> to <8>, which is an external agent for skin.

According to an aspect of the invention, a ceramide dispersion composition which contains a ceramide having an unsaturated double bond in an O-acyl moiety and which is excellent in oxidation stability and dispersion stability is provided.

DETAILED DESCRIPTION OF THE INVENTION

Hereinafter, a description is made of examples of the embodiments of the ceramide dispersion composition to which the invention is applied. Here, the invention is not limited to the following embodiments, but may be appropriately modified and performed within the scope of an object of the invention.

The numerical value range represented using "to" herein means a range including numerical values described before and after the "to" as the minimum value and the maximum value, respectively.

The amount of respective components in the ceramide dispersion composition herein means, in a case in which several substances corresponding to the respective components exist in the ceramide dispersion composition, a total amount of the several substances existing in the ceramide dispersion composition, unless otherwise specified in particular.

The term "process" herein includes not only an independent step but also a process by which a desired object in the process is achieved even in a case in which the process cannot be definitely distinguished from another process.

<Ceramide Dispersion Composition>

A ceramide dispersion composition according to an embodiment includes: at least one ceramide (hereinafter also referred to as the "specific ceramide") represented by the following Formula (1) or Formula (2); a surfactant; and trisodium ascorbyl palmitate phosphate. In an embodiment, the ceramide dispersion composition may contain another component(s) in addition to the specific ceramide, surfactant, and trisodium ascorbyl palmitate phosphate, if necessary.

The ceramide dispersion composition according to an embodiment takes a form in which dispersed particles including the specific ceramide (hereinafter also referred to as the "ceramide-containing particles") are dispersed as a dispersion phase in a continuous phase.

The ceramide dispersion composition according to an embodiment contains the specific ceramide, the oxidation stability of which is poor and the dispersion stability of which is hard to be kept, along with a surfactant and trisodium ascorbyl palmitate phosphate, whereby the composition exerts superior oxidation stability and dispersion stability.

Here, as a result of examination made by the inventors, it becomes clear that the dispersion stability remarkably decreases in a case in which ascorbyl palmitate, sodium ascorbate, sodium ascorbyl phosphate, or magnesium ascorbyl phosphate is used as an antioxidizing agent, instead of trisodium ascorbyl palmitate phosphate. In addition, as a result of examination made by the inventors, it becomes clear that, in comparison with a case in which an antioxidizing agent is not used, the oxidation stability decreases in a case in which tocopherol is used as an antioxidizing agent instead of trisodium ascorbyl palmitate phosphate. It is surprising that a ceramide dispersion composition having superior oxidation stability and dispersion stability is obtained when trisodium ascorbyl palmitate phosphate is used.

Hereinafter, a detailed description is made of the component(s) which may be included in the ceramide dispersion composition.

(Specific Ceramide)

The ceramide dispersion composition according to an embodiment contains at least one ceramide (i.e., specific ceramide) represented by the following Formula (1) or Formula (2).

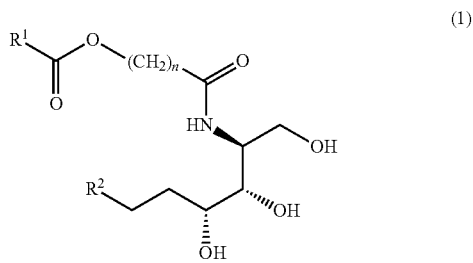

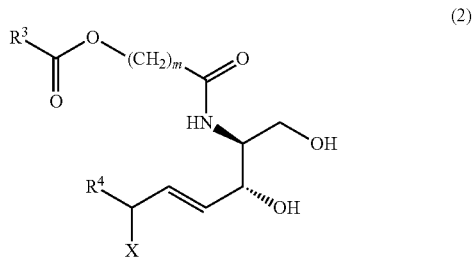

In Formulae (1) and (2), $R^1$ and $R^3$ each independently represent an aliphatic hydrocarbon group having at least one unsaturated double bond.

The number of carbon atoms in the aliphatic hydrocarbon group is preferably 15 or more, more preferably from 15 to 23, still more preferably from 15 to 19, and particularly preferably 17. The aliphatic hydrocarbon group may be straight-chained or branched-chained, and is preferably straight-chained. The number of unsaturated double bonds which the aliphatic hydrocarbon group has is preferably from 1 to 3, and more preferably 1 or 2.

The aliphatic hydrocarbon groups represented by $R^1$ and $R^3$ may further have a substituent, respectively. Examples of the substituent in the aliphatic hydrocarbon group include a hydroxyl group and a carbonyl group. Note that the number of carbon atoms of the aliphatic hydrocarbon group does not include the number of carbon atoms of the substituent.

Specific examples of $R^1$ or $R^3$ include any group which results in palmitoleic acid, sapienic acid, oleic acid, vaccenic acid, gadoleic acid, eicosenoic acid, erucic acid, nervone acid, linoleic acid, eicosadienoic acid, docosadienoic acid, α-linolenic acid, β-linolenic acid, pinolenic acid, α-eleostearic acid, β-eleostearic acid, Mead acid, dihomo-γ-linolenic acid, or eicosatriene acid when represented by $R^1COOH$ or $R^3COOH$. Among them, a group which results in oleic acid, linoleic acid, α-linolenic acid, or β-linolenic acid is more preferable, and a group which results in oleic acid or linoleic acid is still more preferable.

In Formulae (1) and (2), $R^2$ and $R^4$ each independently represent an alkyl group having 9 or more carbon atoms. The number of carbon atoms in the alkyl group is preferably from 9 to 19, more preferably from 11 to 19, and still more preferably from 12 to 18. The alkyl group may be straight-chained or branched-chained, and is preferably straight-chained.

In Formulae (1) and (2), n and m each independently represent an integer from 20 to 34, preferably an integer from 24 to 30, more preferably an integer from 26 to 28, and still more preferably 26.

In Formula (2), X represents a hydrogen atom or a hydroxyl group, and preferably represents a hydrogen atom.

Examples of a suitable combination of $R^1$, $R^2$, and n in Formula (1) include any combination of the above-mentioned suitable aspects of $R^1$, $R^2$ and n. Examples of a suitable combination of $R^3$, $R^4$, m and X in Formula (2) include any combination of the above-mentioned suitable aspects of $R^3$, $R^4$, m and X.

Examples of the specific ceramide include natural type ceramides known as acyl-ceramides.

The "natural type ceramide" herein means a ceramide having the same structure as that of the ceramide existing in a horny cell layer of human skin.

The natural type ceramide may be a natural product (for example, an extract) or a ceramide obtained by a microbial fermentation method, or may be a synthetic product or an animal-derived ceramide.

The specific ceramide may include both of a natural type ceramide and a non-natural type ceramide, if necessary. In a case in which the specific ceramide includes both of a natural type ceramide and a non-natural type ceramide, it is preferable that the proportion of the natural type ceramide is higher than that of the non-natural type ceramide, in order to enhance the skin barrier effect.

Examples of the natural type ceramide usable as the specific ceramide include ceramide EOP (ceramide 9), ceramide EOS (ceramide 1), and ceramide EOH (ceramide 4).

Such a natural type ceramide is available as a commercial product. Examples of commercial product of the natural type ceramide include Ceramide EOP and Ceramide EOS.

Hereinafter, specific examples of the specific ceramide are given. However, the specific ceramide is not limited to the following specific examples.

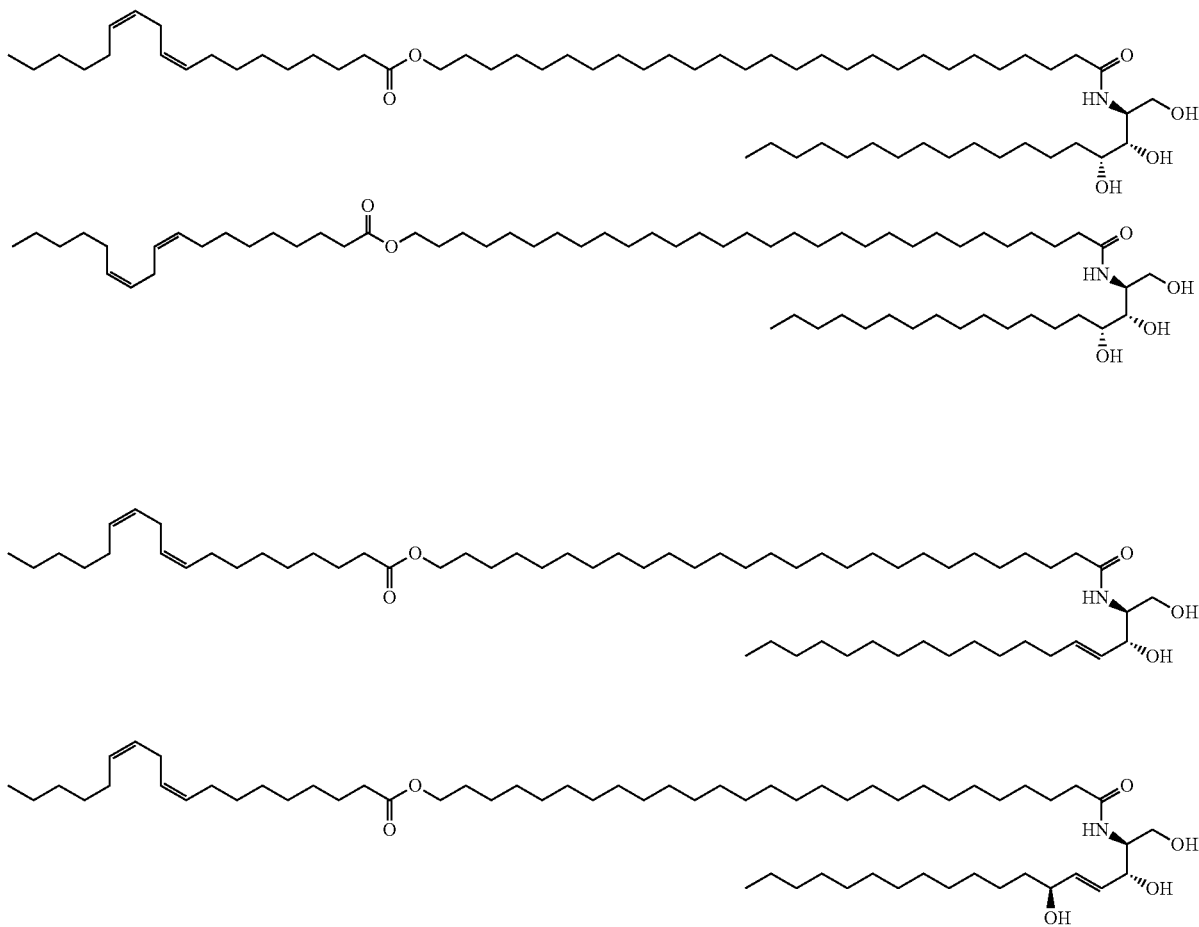

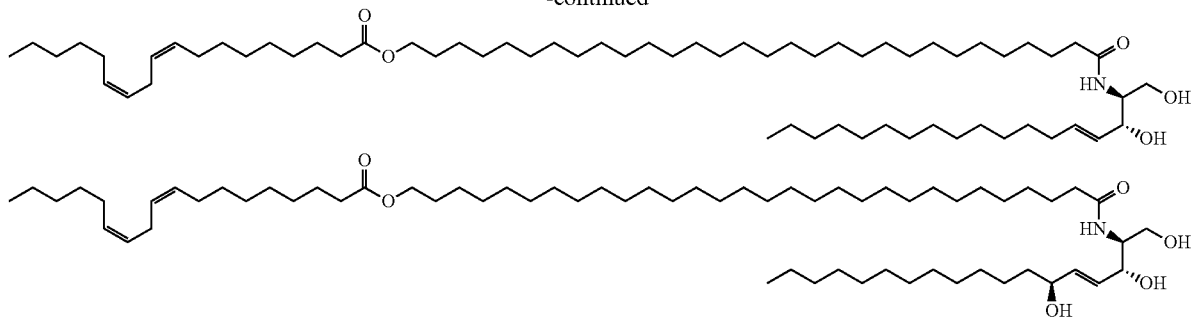

The ceramide dispersion composition according to an embodiment may contain one kind of specific ceramide, or may contain a combination of two or more kinds of specific ceramides.

In an embodiment, the ceramide dispersion composition may further contain a ceramide other than the specific ceramide as long as the effect of the disclosure is not deteriorated.

From the viewpoint of the skin care effect in a case in which the ceramide dispersion composition is applied to an external agent for skin, the content of specific ceramide in the ceramide dispersion composition with respect to the total mass of ceramide dispersion composition is, for example, preferably from 0.00001% by mass to 10% by mass, more preferably from 0.00003% by mass to 5% by mass, still more preferably from 0.0001% by mass to 1% by mass, particularly preferably from 0.01% by mass to 1% by mass, and most preferably from 0.1% by mass to 1% by mass.

(Surfactant)

The ceramide dispersion composition according to an embodiment contains a surfactant. The surfactant is not limited in particular, and examples thereof include a nonionic surfactant, a cationic surfactant, an anionic surfactant, and an amphoteric surfactant. Among such surfactants, a nonionic surfactant is preferable, from the viewpoints of micronization of the dispersed particles and dispersion stability.

Examples of the nonionic surfactant include glycerol fatty acid esters, polyglycerol fatty acid esters, organic acid monoglycerides, propylene glycol fatty acid esters, polyglycerol condensed ricinoleic acid esters, sorbitan fatty acid esters, sucrose fatty acid esters, and polyoxyethylene sorbitan fatty acid esters. These nonionic surfactants need not be a highly purified nonionic surfactant obtained through distillation or the like, and may be a reaction mixture.

Among the above-mentioned examples, the nonionic surfactant is preferably a polyglycerol fatty acid ester, and more preferably a polyglycerol fatty acid ester having an HLB (Hydrophile-Lipophile Balance) of from 10 to 16, from the viewpoints of micronization of the dispersed particles and dispersion stability. The polyglycerol fatty acid ester is capable of largely reducing the interfacial tension between the dispersion phase and the continuous phase, thereby further micronizing the dispersed particles.

HLB means the balance between hydrophilicity and hydrophobicity generally used in the field of surfactant. HLB may be calculated using a generally used calculation formula such as Kawakami equation. Herein, the following Kawakami equation is employed.

$$HLB = 7 + 11.7 \log (Mw/Mo)$$

Mw is the molecular weight of a hydrophilic group, and Mo is the molecular weight of a hydrophobic group.

As the HLB of a polyglycerol fatty acid ester, numerical values indicated in catalogues or the like may be employed. As is evident from the equation, using the additivity of HLB makes it possible to produce a surfactant having any HLB value.

At least one polyglycerol fatty acid ester is preferably an ester of a polyglycerol having an average degree of polymerization of 10 with a fatty acid having 8 to 18 carbon atoms, such as a fatty acid selected from the group consisting of caprylic acid, capric acid, lauric acid, myristic acid, palmitic acid, stearic acid, oleic acid, and linoleic acid.

More preferable examples of the polyglycerol fatty acid ester include hexaglycerol monooleic acid ester, hexaglycerol monopalmitic acid ester, hexaglycerol monomyristic acid ester, hexaglycerol monolauric acid ester, decaglycerol monolinoleic acid ester, decaglycerol monooleic acid ester, decaglycerol monostearic acid ester, decaglycerol monopalmitic acid ester, decaglycerol monomyristic acid ester, and decaglycerol monolauric acid ester. The HLBs of the polyglycerol fatty acid esters are from 10 to 16.

As the polyglycerol fatty acid ester, at least one selected from the group consisting of decaglycerol monolinoleic acid ester (HLB=12), decaglycerol monooleic acid ester (HLB=12), decaglycerol monostearic acid ester (HLB=12), decaglycerol monopalmitic acid ester (HLB=13), decaglycerol monomyristic acid ester (HLB=14), and decaglycerol monolauric acid ester (HLB=16) is still more preferable, and decaglycerol monomyristic acid ester is particularly preferable.

As the polyglycerol fatty acid ester, a combination of one or more selected from polyglycerol fatty acid esters having HLBs of from 10 to 16 and one or more selected from polyglycerol fatty acid esters having HLBs of from 5 to 15, the molecular structures of which are different from each other, may be used.

As the polyglycerol fatty acid ester, a commercial product may also be used. Examples of the commercial product of polyglycerol fatty acid ester include NIKKOL (registered trademark) DGMS, DGMO-CV, DGMO-90V, DGDO, DGMIS, DGTIS, TETRAGLYN 1-SV, TETRAGLYN 1-O, TETRAGLYN 3-S, TETRAGLYN 5-S, TETRAGLYN 5-O, HEXAGLYN 1-L, HEXAGLYN 1-M, HEXAGLYN 1-SV, HEXAGLYN 1-O, HEXAGLYN 3-S, HEXAGLYN 4-B, HEXAGLYN 5-S, HEXAGLYN 5-O, HEXAGLYN PR-15, DECAGLYN 1-L, DECAGLYN 1-M, DECAGLYN 1-SV, DECAGLYN 1-50SV, DECAGLYN 1-ISV, DECAGLYN 1-O, DECAGLYN 1-OV, DECAGLYN 1-LN, DECAGLYN 2-SV, DECAGLYN 2-ISV, DECAGLYN 3-SV, DECAGLYN 3-OV, DECAGLYN 5-SV, DECAGLYN 5-HS, DECAGLYN 5-IS, DECAGLYN 5-OV, DECAGLYN 5-O-R, DECAGLYN 7-S, DECAGLYN 7-O, DECAGLYN 10-SV, DECAGLYN 10-IS, DECAGLYN 10-OV, DECAGLYN 10-MAC, and DECAGLYN PR-20 (all of which are available from NIKKO CHEMICALS CO., LTD.); RYOTO (registered trademark) POLYGLYESTER L-7D, L-10D, M-10D, P-8D, SWA-10D, SWA-15D, SWA-20D, S-24D, S-28D, O-15D, O-50D, B-70D, B-100D, ER-60D, LOP-120DP, DS13W, DS3, HS11, HS9, TS4, TS2, DL15, and DO13 (all of which are available from MITSUBISHI-KAGAKU FOODS CORPORATION); SUNSOFT (registered trademark) Q-17UL, Q-14S, and A-141C (all of which are available from TAIYO KAGAKU CO., LTD.); and POEM (registered trademark) DO-100 and J-0021 (all of which are available from RIKEN VITAMIN CO., LTD.).

Among them, preferable commercial products of the polyglycerol fatty acid ester are NIKKOL (registered trademark) DECAGLYN 1-L, DECAGLYN 1-M, DECAGLYN 1-SV, DECAGLYN 1-50SV, DECAGLYN 1-ISV, DECAGLYN 1-O, DECAGLYN 1-OV and DECAGLYN 1-LN, and RYOTO (registered trademark) POLYGLYESTER L-7D, L-10D, M-10D, P-8D, SWA-10D, SWA-15D, SWA-20D, S-24D, S-28D, O-15D, O-50D, B-70D, B-100D, ER-60D and LOP-120DP.

In an embodiment, the ceramide dispersion composition may contain one kind of surfactant, or may contain a combination of two or more kinds of surfactants.

The content of surfactant in the ceramide dispersion composition of this embodiment with respect to the content of specific ceramide is, for example, preferably from 1 time by mass to 70 times by mass, more preferably from 3 times by mass to 40 times by mass, still more preferably from 5 times by mass to 20 times by mass, from the viewpoints of micronization of the dispersed particles and dispersion stability.

(Trisodium Ascorbyl Palmitate Phosphate)

The ceramide dispersion composition according to an embodiment contains trisodium ascorbyl palmitate phosphate. Since the ceramide dispersion composition contains trisodium ascorbyl palmitate phosphate, the oxidation stability of the specific ceramide tends to be enhanced.

As trisodium ascorbyl palmitate phosphate, a commercial product may be used. Examples of the commercial product of trisodium ascorbyl palmitate phosphate include APPRECIER (registered trademark) available from SHOWA DENKO K.K.

The content of trisodium ascorbyl palmitate phosphate in the ceramide dispersion composition according to an embodiment with respect to the content of the specific ceramide is, for example, preferably from 1 time by mass to 8 times by mass, more preferably from 1 time by mass to 4 times by mass, and still more preferably from 1 time by mass to 2 times by mass, from the viewpoints of oxidation stability of the specific ceramide, and micronization of the dispersed particles and dispersion stability.

(Lecithin)

In an embodiment, it is preferable that the ceramide dispersion composition further contains lecithin. When the ceramide dispersion composition contains lecithin in addition to a surfactant (preferably a nonionic surfactant), the dispersed particles tend to be further micronized.

Since lecithin has a hydrophilic group and a hydrophobic group in a molecule thereof, lecithin has been conventionally used as an emulsifier in various fields of foods, medicines, cosmetics and the like. Industrially, a lecithin having a lecithin purity of 60% by mass or higher is used as the lecithin, and such a lecithin having a lecithin purity of 60% by mass or higher may be used in the ceramide dispersion composition according to an embodiment. From a viewpoint of forming more finely dispersed particles, the lecithin is preferably a lecithin having a lecithin purity of 80% by mass or higher, and more preferably a lecithin having a lecithin purity of 90% by mass or higher, which are generally referred to as "high-purity lecithin".

Examples of the lecithin include publicly known various lecithins extracted and separated from living bodies of plant, animal, and microorganism.

Specific examples of the lecithin include various lecithins derived from a plant such as soybean, corn, peanut, rape seed or wheat, an animal such as egg yolk or cattle, and a microorganism such as *Escherichia coli*.

Examples of the compound name of such lecithins include glycero lecithins such as phosphatidic acid, phosphatidylglycerol, phosphatidylinositol, phosphatidylethanolamine, phosphatidylmethylethanolamine, phosphatidylcholine, phosphatidylserine, bisphosphatidic acid, or diphosphatidylglycerol (cardiolipin); and sphingolecithins such as sphingomyelin.

In the ceramide dispersion composition according to an embodiment, other lecithin(s) than the above-mentioned high-purity lecithin, such as a hydrogenated lecithin, an enzymatically-decomposed lecithin, an enzymatically-decomposed hydrogenated lecithin, or a hydroxy lecithin may be used. In the ceramide dispersion composition, lecithins may be used singly, or in a mixture of two or more thereof.

In a case in which the ceramide dispersion composition contains lecithin, the content of lecithin with respect to the content of surfactant is, for example, preferably from 0.01 times by mass to 20 times by mass, more preferably from 0.1 times by mass to 10 times by mass, and still more preferably from 0.4 times by mass to 5 times by mass, from the viewpoint of micronization of the dispersed particles.

In a preferable embodiment of the ceramide dispersion composition, the content of surfactant with respect to the content of specific ceramide is from 1 time by mass to 70 times by mass (preferably from 3 times by mass to 40 times by mass, and more preferably from 5 times by mass to 20 times by mass), and the content of lecithin with respect to the content of surfactant is from 0.01 times by mass to 20 times by mass (preferably from 0.1 times by mass to 10 times by mass, and more preferably from 0.4 times by mass to 5 times by mass).

(Cholesterol)

The ceramide dispersion composition according to an embodiment may further contain cholesterol. When the ceramide dispersion composition contains cholesterol, the skin care effect tends to improve in a case in which the ceramide dispersion composition is applied to an external agent for skin.

As the cholesterol, a cholesterol purified from raw cholesterol obtained from lanoline through extraction may be preferably applied. As the cholesterol, a commercial product may also be used. Examples of the commercial product of cholesterol include CHOLESTEROL JSQI available from NIPPON FINE CHEMICAL CO., LTD.; and cholesterols available from Croda Japan KK.

In a case in which the ceramide dispersion composition contains cholesterol, the content of cholesterol may be appropriately set, taking the effect expected by containing cholesterol into consideration. The content of cholesterol with respect to the total mass of ceramide dispersion composition is, for example, preferably from 0.00001% by mass to 10% by mass, more preferably from 0.00003% by mass to 5% by mass, and still more preferably from 0.0001% by mass to 1% by mass.

(Polyhydric Alcohol)

The ceramide dispersion composition according to an embodiment may further contain a polyhydric alcohol.

The polyhydric alcohol is not particularly limited as long as the polyhydric alcohol is a polyhydric alcohol such as a dihydric or higher-hydric alcohol, and a publicly known polyhydric alcohol may be used.

Examples of the polyhydric alcohol include glycerol, diglycerol, triglycerol, polyglycerol, diol compounds (such as 1,3-butylene glycol, isoprene glycol, polyethylene glycol, propylene glycol, polypropylene glycol, ethylene glycol, diethylene glycol, neopentyl glycol, 1,2-pentanediol, 1,2-hexanediol, dipropylene glycol, or 3-methyl-1,3-butanediol), maltitol, reduced starch syrup, sucrose, lactitol, palatinit, erythritol, sorbitol, mannitol, xylitol, xylose, glucose, lactose, mannose, maltose, galactose, fructose, inositol, pentaerythritol, maltotriose, sorbitan, trehalose, starch-decomposed sugar, and starch-decomposed sugar-reduced alcohol.

Among them, the polyhydric alcohol is preferably at least one selected from the group consisting of glycerol and diol compounds, and more preferably glycerol and at least one diol compound, from the viewpoint of micronization of the dispersed particles. In particular, in a case in which a combination of glycerol and at least one diol compound is used for the polyhydric alcohol, it is capable to allow the ceramide dispersion composition to contain more finely dispersed particles.

When the ceramide dispersion composition contains glycerol and at least one diol compound, the mass ratio between glycerol and diol compound (i.e., glycerol/diol compound) is, for example, preferably from 100/1 to 1/1, more preferably from 75/1 to 5/1, still more preferably from 50/1 to 10/1, from the viewpoint of micronization of the dispersed particles.

From the viewpoints of micronization and dispersion stability of the dispersed particles, the diol compound is preferably at least one selected from the group consisting of 1,3-butylene glycol, dipropylene glycol, 1,4-butylene glycol, diethylene glycol, ethylene glycol, propylene glycol, 1,2-pentanediol, 1,4-pentanediol, 1,5-pentanediol, 2,4-pentanediol, 1,2-hexanediol, and 1,6-hexanediol, more preferably at least one selected from the group consisting of 1,3-butylene glycol and dipropylene glycol, and still more preferably 1,3-butylene glycol.

In a case in which the ceramide dispersion composition contains a polyhydric alcohol, the content of polyhydric alcohol with respect to the total mass of ceramide dispersion composition is, for example, preferably from 1% by mass to 70% by mass, more preferably from 5% by mass to 65% by mass, and still more preferably from 10% by mass to 60% by mass, from the viewpoints of micronization of the dispersed particles and dispersion stability.

(Water or Water-Containing Composition)

The ceramide dispersion composition according to an embodiment takes a form in which the dispersed particles including the specific ceramide are dispersed as a dispersion phase in a continuous phase. It is preferable that the continuous phase is water or a water-containing composition (hereinafter also referred to as "water or the like").

It is preferable that the water is water having few impurities such as pure water or ion exchanged water.

The "water-containing composition" herein merely means that it is satisfactory for the composition to contain water. A component other than water to be included in the composition is not limited in particular, and examples thereof include publicly known water-soluble components which may be generally added in a continuous phase in a dispersion composition.

(Other Components)

In some embodiments, the ceramide dispersion composition may further contain component(s) other than the above-mentioned components, if necessary, as long as the effect of the disclosure is not deteriorated.

Examples of such other component(s) include components which may be generally added in a dispersion composition, and components required depending on the use of a ceramide dispersion composition to be obtained.

Examples of such other component(s) in a case in which the ceramide dispersion composition is applied to an external agent for skin include various kinds of pharmaceutical components, preservatives (such as iodopropynyl butyl carbamate), fungicides, coloring agents, refreshing agents (such as menthol or camphor), plant extracts, pH buffers, antioxidizing agents, UV absorbers, UV scatterers, and aromatics.

(Oily Component which is Liquid at 25° C.)

In some embodiments, it is preferable that a content of an oily component which is liquid at 25° C. in the ceramide dispersion composition is 1% by mass or lower, or that the ceramide dispersion composition does not contain an oily component which is liquid at 25° C., and more preferable that the ceramide dispersion composition does not contain an oily component which is liquid at 25° C. In the case in which the content of oily component which is liquid at 25° C. is 1% by mass or lower or the ceramide dispersion composition does not contain an oily component which is liquid at 25° C., it is capable of allowing the ceramide dispersion composition to include more finely dispersed particles.

The "liquid at 25° C." herein means that the melting point or softening point is less than 25° C. In addition, the "oily component" herein means a component which has a solubility in water at 25° C. of less than 0.1% by mass, and which is generally used as an oily component in the fields of cosmetics, medicines, foods or the like.

Examples of the oily component which is liquid at 25° C. include hydrocarbon oils such as squalane or liquid paraffin; silicone oils such as dimethylpolysiloxane, dimethylcyclopolysiloxane, methylphenylpolysiloxane, methylhydrogenpolysiloxane, or higher alcohol-modified organopolysiloxane; fluorine-containing oils such as fluoropolyether or perfluoroalkylether silicone; vegetable oils such as olive oil or jojoba oil; animal oils such as liquid lanoline; fatty acid esters such as diisostearyl malate, octyldodecyl lactate, isotridecyl isononanoate, isopropyl isostearate, or octyldodecyl myristate; ester oils consisting of a fatty acid and a polyhydric alcohol such as neopentyl glycol dicaprate; and ester oils of a glycerol derivative, an amino acid derivative, or the like.

(Particle Diameter of Dispersed Particles)

The average particle diameter of the dispersed particles included in the ceramide dispersion composition according to an embodiment is, for example, preferably 200 nm or less, more preferably 100 nm or less, and still more preferably 40 nm or less, from the viewpoint of skin care effect when the ceramide dispersion composition is applied to an external agent for skin. The lower limit of the average particle diameter of the dispersed particles is not limited in particular. The average particle diameter of the dispersed particles may be, for example, 1 nm or more.

The average particle diameter of the dispersed particles herein means a volume average particle diameter of the dispersed particles existing in the ceramide dispersion composition.

The volume average particle diameter of the dispersed particles is preferably measured by a dynamic light scattering method, from the viewpoints of accuracy and convenience of measurement.

A commercial measuring device using a dynamic light scattering method is not limited in particular, and examples thereof include dynamic light scattering nanotrac particle size analyzer UPA (available from NIKKISO CO., LTD.), dynamic light scattering particle size distribution analyzer LB-550 (available from HORIBA, LTD.), and concentrated-system particle diameter analyzer FPAR-1000 (available from OTSUKA ELECTRONICS CO., LTD.).

The volume average particle diameter of the dispersed particles herein is a value measured using a dynamic light scattering nanotrac particle size analyzer UPA (available from NIKKISO CO., LTD.). Specifically, the volume average particle diameter is measured as follows. The average particle diameter of the dispersed particles may also be measured using another analyzer.

The volume average particle diameter of the dispersed particles is measured using a quartz cell in which the concentration of the specific ceramide included in a sample separately collected from the ceramide dispersion composition according to an embodiment is adjusted to 0.04% by mass through dilution with pure water. Then, the volume average particle diameter can be determined as a volume average particle diameter (Mv) in a case in which the refractive index of the sample is set to 1.600, the refractive index of the dispersion medium is set to 1.333 (pure water), and the viscosity of dispersion medium is set to the viscosity of pure water.

It is possible to adjust the average particle diameter of the dispersed particles in accordance with the formulation of the composition, as well as a factor such as a stirring condition (such as shearing force, temperature, or pressure) in a producing method or the ratio between the oil phase and the aqueous phase.

From the viewpoint of micronization of the dispersed particles, it is preferable that the ceramide dispersion composition according to an embodiment is a dispersion composition prepared by a high-pressure emulsifying method.

Matters regarding the high-pressure emulsifying method and the embodiments of a dispersing treatment by the high-pressure emulsifying method in preparation of the ceramide dispersion composition will be described in the section regarding a method of producing the ceramide dispersion composition.

(pH)

The pH of the ceramide dispersion composition is appropriately set depending on the applied form of the ceramide dispersion composition. In a case in which the ceramide dispersion composition is applied to an external agent for skin, the pH of the ceramide dispersion composition is, for example, preferably from 3 to 10, and more preferably from 5 to 9, from the viewpoints of skin irritation or the like. When the pH is within in the ranges, the skin irritation tends to be reduced and a suitable usability tends to be obtained.

<Method of Producing Ceramide Dispersion Composition>

The ceramide dispersion composition according to an embodiment may be obtained by a producing method including a process of mixing a dispersion phase component containing a specific ceramide and a surfactant, with a continuous phase component containing trisodium ascorbyl palmitate phosphate.

A method of mixing the continuous phase component (aqueous phase component) with the dispersion phase component (oil phase component) is not limited in particular, and a publicly known method such as an ultrasonic dispersing method, a high-pressure emulsifying method, or a jet injecting method of directly injecting a dispersion phase component into a continuous phase component may be used.

Examples of a preferable producing method by which the ceramide dispersion composition is obtained include a method including the processes of: subjecting a pre-dispersing treatment solution containing a specific ceramide and a surfactant to a dispersing treatment in a state in which the pre-dispersing treatment solution is heated to 100° C. or higher to prepare a coarse dispersion (hereinafter also referred to as "preliminary dispersing treatment process"); and subjecting a mixture obtained by mixing the coarse dispersion with water or the like containing trisodium ascorbyl palmitate phosphate to a dispersing treatment by an ultrasonic dispersing method or a high-pressure emulsifying method (hereinafter also referred to as "main dispersing treatment process").

Hereinafter, a description is made of a producing method of this aspect.

(Preliminary Dispersing Treatment Process)

In preparation of the coarse dispersion in the preliminary dispersing treatment process, a dispersing treatment is performed while a solution containing a specific ceramide and a surfactant (i.e., a pre-dispersion treatment solution) is heated to 100° C. or higher, whereby a coarse dispersion in which the dispersed particles (i.e., dispersion phase) including the specific ceramide in a meltdown state due to the heating are coarsely dispersed in a continuous phase is obtained.

In the pre-dispersing treatment solution, it is satisfactory for the specific ceramide and the surfactant to simply be mixed with each other. A method of mixing the specific ceramide and the surfactant is not limited in particular, and examples thereof include a mixing method by stirring.

The pre-dispersing treatment solution may also contain other component(s) in addition to the specific ceramide and surfactant, if necessary. Examples of such other component(s) include a component such as a polyhydric alcohol or cholesterol.

In preparation of the coarse dispersion, the pre-dispersing treatment solution is heated to 100° C. or higher, in order to melt the specific ceramide. It is satisfactory in the invention that the temperature of 100° C. or higher is achieved during the dispersing treatment of the pre-dispersing treatment solution. The dispersing treatment may be performed in a state in which the pre-dispersing treatment solution is preliminarily heated to 100° C. or higher and the solution temperature is maintained at 100° C. or higher, or the dispersing treatment may also be performed while the pre-dispersing treatment solution is heated to 100° C. or higher.

A means for heating the pre-dispersing treatment solution to 100° C. or higher is not limited in particular, and examples thereof may include a general heating device. Examples of the heating device include a thermostatic chamber.

A means for performing the dispersing treatment of the pre-dispersing treatment solution to prepare the coarse dispersion is not limited in particular, and examples thereof include a general agitator. Examples of the agitator include a magnetic stirrer, a mixer for household use, a paddle mixer, an impeller mixer, a homomixer, a disper-mixer, or an ultra mixer.

The time period for the dispersing treatment is not limited in particular, and may be appropriately set depending on the type of agitator, the formulation of the pre-dispersing treatment solution, or the like.

(Main Dispersing Treatment Process)

In the main dispersing treatment process, the coarse dispersion obtained by the preliminary dispersing treatment is mixed with water or the like containing trisodium ascorbyl palmitate phosphate, and then a dispersing treatment by an ultrasonic dispersing method (hereinafter referred to as an "ultrasonic dispersing treatment") or a dispersing treatment by a high-pressure emulsifying method (hereinafter referred to as a "high-pressure emulsifying treatment") may be performed.

In the main dispersing treatment process, the coarse dispersion containing the melted specific ceramide and surfactant is mixed with water or the like containing trisodium ascorbyl palmitate phosphate, followed by the dispersing treatment, whereby a ceramide dispersion composition including the dispersed particles containing the specific ceramide is obtained.

The temperature of the coarse dispersion during the mixing with water or the like is preferably set to 100° C. or lower, and more preferably set to from 90° C. to 100° C., from the viewpoint of preventing bumping.

The temperature of water or the like is not limited in particular. The temperature of water or the like is preferably set to from 50° C. to 90° C.

The coarse dispersion and water or the like may be mixed with each other at one time, or may be mixed with each other while one of them is gradually added to the other. It is satisfactory for the coarse dispersion and water or the like to simply be mixed with each other. Examples of a method of mixing the coarse dispersion with water or the like include a mixing method by stirring.

The mixing ratio between the coarse dispersion and water or the like is not limited in particular. From the viewpoint of micronizing the dispersed particles, the ratio of coarse dispersion/water or the like (in terms of mass) is, for example, preferably from 1/20 to 10/1, more preferably from 1/10 to 5/1, and still more preferably from 1/2 to 2/1.

The coarse dispersion and water or the like are mixed with each other such that the ratio between the dispersion phase and the continuous phase in the ceramide dispersion composition as the ratio of dispersion phase/continuous phase (in terms of mass) is preferably from 1/1000 to 1/5, more preferably from 1/100 to 1/10, and still more preferably from 1/50 to 1/10, from the viewpoints of micronization of the dispersed particles and dispersion stability.

As the dispersing treatment in the main dispersing treatment process, a high-pressure emulsifying treatment is preferable, from the viewpoint of micronization of the dispersed particles.

A high-pressure emulsifying treatment herein means a dispersing treatment for applying a shearing force of 50 MPa or more to an object to be dispersed. From the viewpoint of micronization of the dispersed particles, the shearing force applied to an object to be dispersed is preferably 100 MPa or more, and more preferably 180 MPa or more. In a case in which a commercial device is used, the upper limit of the shearing force applied to an object to be dispersed is about 300 MPa, from the viewpoints of temperature rise and pressure resistance.

A means for high-pressure emulsifying treatment is not limited in particular, and examples thereof include a general high-pressure emulsifying device. Examples of the high-pressure emulsifying device include high-pressure homogenizers such as an ultimizer HJP-25005 (available from SUGINO MACHINE LIMITED), a microfluidizer (available from MICROFLUIDICS), a nanomizer (available from YOSHIDA KIKAI CO., LTD.), a Gaulin-type homogenizer (available from APV), a Rannie-type homogenizer (available from RANNIE), a high-pressure homogenizer (available from GEA NIRO SOAVI), a homogenizer (available from SANWA ENGINEERING LTD.), a high-pressure homogenizer (available from IZUMI FOOD MACHINERY CO., LTD.), or a ultra high-pressure homogenizer (available from IKA).

The temperature during the high-pressure emulsifying treatment is preferably set to from 20° C. to 80° C., and more preferably set to from 40° C. to 70° C.

The number of times of performing the high-pressure emulsifying treatment may be one time. In order to enhance uniformity of the whole solution, the high-pressure emulsifying treatment is performed preferably two times or more, more preferably from two times to five times. From the viewpoint of retention of the particle diameter of the dispersed particles, an emulsified solution which is the emulsified and dispersed composition is preferably cooled through some kind of refrigerator within 30 seconds, preferably within 3 seconds immediately after passing through the chamber.

The dispersing treatment in the main dispersing treatment process may also be an ultrasonic dispersing treatment. In addition, from the viewpoint of further enhancing the dispersing effect, it is preferable to perform an ultrasonic dispersing treatment after the mixing of the coarse dispersion with water or the like and before the high-pressure emulsifying treatment. A general ultrasonic dispersion device may be used for the ultrasonic dispersing treatment.

Examples of the ultrasonic dispersion device include an ultrasonic homogenizer US-600, US-1200T, RUS-1200T or MUS-1200T (all of which are available from NIHONSEIKI KAISHA LTD.), and an ultrasonic processor UIP2000, UIP4000, UIP8000 or UIP16000 (all of which are available from HIELSCHER ULTRASONICS GmbH). The ultrasonic dispersion devices may be used at a frequency of 25 kHz or less, and preferably from 15 kHz to 20 kHz.

(Other Processes)

The method of producing a ceramide dispersion composition may further include other process(es), in addition to the preliminary dispersing treatment process and the main dispersing treatment process, if necessary. Examples of such other process include a heat-sterilizing process.

<Use of Ceramide Dispersion Composition>

The ceramide dispersion composition may be widely applied to an external agent for skin (such as a pharmaceutical product or a cosmetic agent), a cleaning agent, or the like, and preferably applied to an external agent for skin.

Examples of the pharmaceutical product include a parenteral agent such as a liniment. Examples of the cosmetic agent include a lotion, beauty essence, gel, emulsion, hair conditioner, hair treatment, and rinse. Examples of the cleaning agent include a face wash, body soap, and shampoo. Note that use of the ceramide dispersion composition is not limited thereto.

In a case in which the ceramide dispersion composition is used in a pharmaceutical product or cosmetic agent, a component(s) capable of being added to a pharmaceutical product or cosmetic agent may be appropriately added, if necessary.

EXAMPLES

Hereinafter, more specific description is made of the invention with reference to Examples. The invention is not limited to the following Examples unless the invention is beyond the gist of the present disclosure. The "part" is in terms of mass, unless otherwise specified in particular.

Example 1

First, 40.5 g of solution A having the following formulation was stirred and mixed at 110° C. for 10 minutes, to thereby obtain a coarse dispersion. The obtained coarse dispersion was cooled to 100° C., and solution B which was obtained by dissolving the following components at 70° C. was added thereto. Then, the resultant was subjected to dispersion using an ultrasonic homogenizer US-600 (available from NIHONSEIKI KAISHA LTD.) for 3 minutes, to thereby obtain a preliminary dispersion. Subsequently, the obtained preliminary dispersion was cooled to about 60° C., followed by performing a high-pressure emulsifying (dispersing) treatment 5 times at a pressure of 245 MPa using an ultimizer HJP-25005 (available from SUGINO MACHINE LIMITED), thereby obtaining a ceramide dispersion composition of Example 1.

The details of the respective components used in solution A and solution B are as follows.

[Solution A]
Ceramide A 0.3 parts
Cholesterol 0.3 parts
1,3-Butylene glycol 0.9 parts
Decaglycerol monomyristic acid ester 4.0 parts
Glycerol 35.0 parts
[Solution B]
Lecithin 4.0 parts
Trisodium ascorbyl palmitate phosphate 0.5 parts
Iodopropynyl butyl carbamate 0.015 parts
Ion exchanged water 55.5 parts Examples 2 and 3

A ceramide dispersion composition of each of Examples 2 and 3 was obtained in the same manner as Example 1, except that the mixing amount of trisodium ascorbyl palmitate phosphate was changed as shown in Table 1.

Example 4

A ceramide dispersion composition of Example 4 was obtained in the same manner as Example 1, except that lecithin was not used.

Example 5

A ceramide dispersion composition of Example 5 was obtained in the same manner as Example 1, except that ceramide B was used instead of ceramide A.

Example 6

A ceramide dispersion composition of Example 6 was obtained in the same manner as Example 1, except that the mixing amount of trisodium ascorbyl palmitate phosphate was changed as shown in Table 1.

Comparative Example 1

A ceramide dispersion composition of Comparative Example 1 was obtained in the same manner as Example 1, except that trisodium ascorbyl palmitate phosphate was not used.

Comparative Examples 2 to 11

A ceramide dispersion composition of each of Comparative Examples 2 to 11 was obtained in the same manner as Example 1, except that ascorbyl palmitate, sodium ascorbate, sodium ascorbyl phosphate, magnesium ascorbyl phosphate, or tocopherol was used in the mixing amount as shown in Table 2 instead of trisodium ascorbyl palmitate phosphate. Here, ascorbyl palmitate and tocopherol were used in solution A, and sodium ascorbate, sodium ascorbyl phosphate and magnesium ascorbyl phosphate were used in solution B.

Reference Example 1

A ceramide dispersion composition of Reference Example 1 was obtained in the same manner as Example 2, except that ceramide C was used instead of ceramide A.

Reference Example 2

A ceramide dispersion composition of Reference Example 2 was obtained in the same manner as Example 2, except that ceramide D was used instead of ceramide A.

The formulations of the respective ceramide dispersion compositions of Examples 1 to 6, Comparative Examples 1 to 11, and Reference Examples 1 and 2 are shown in Tables 1 to 3. In Tables 1 to 3, the item "-" in the column regarding the formulation means that the component is not added.

Here, Example 2 or 5 is duplicated in Tables 1 and 3 for convenience of comparison, and thus the duplicated ones are the same as each other.

The details of the respective components in Tables 1 to 3 are as follows. Structural Formulae of ceramides A to D are also shown.

Trisodium ascorbyl palmitate phosphate (trade name: APPRECIER (registered trademark), SHOWADENKO K.K.)
Ascorbyl palmitate (trade name: L-ASCORBYL PALMITATE, DSM NUTRITION JAPAN K.K.)
Sodium ascorbate (trade name: SODIUM ASCORBATE, BASF JAPAN LTD.)
Sodium ascorbyl phosphate (trade name: ASCORBYL PHOSPHATE SODIUM, SHOWA DENKO K.K.)
Magnesium ascorbyl phosphate (trade name: C-MATE, BASF JAPAN LTD.)
Tocopherol (trade name: RIKEN E-OIL 800, RIKEN VITAMIN CO., LTD.)
Decaglycerol monomyristic acid ester (trade name: NIKKOL (registered trademark) DECAGLYN 1-M, HLB: 14.0, NIKKO CHEMICALS CO., LTD.)
Lecithin (trade name: SLP-PC70, TSUJI OIL MILLS CO., LTD.)
Cholesterol (trade name: CHOLESTEROL JSQI, NIPPON FINE CHEMICAL CO., LTD.)
1,3-Butylene glycol (DAICEL CORPORATION)

Glycerol (cosmetic concentrated glycerol, KAO CORPORATION)

Iodopropynyl butyl carbamate (trade name: GLYCACIL, LONZA JAPAN)

a manner that the concentration of the ceramide included in a sample separately collected from the ceramide dispersion composition is adjusted to 0.04% by mass by dilution with pure water. The volume average particle diameter was

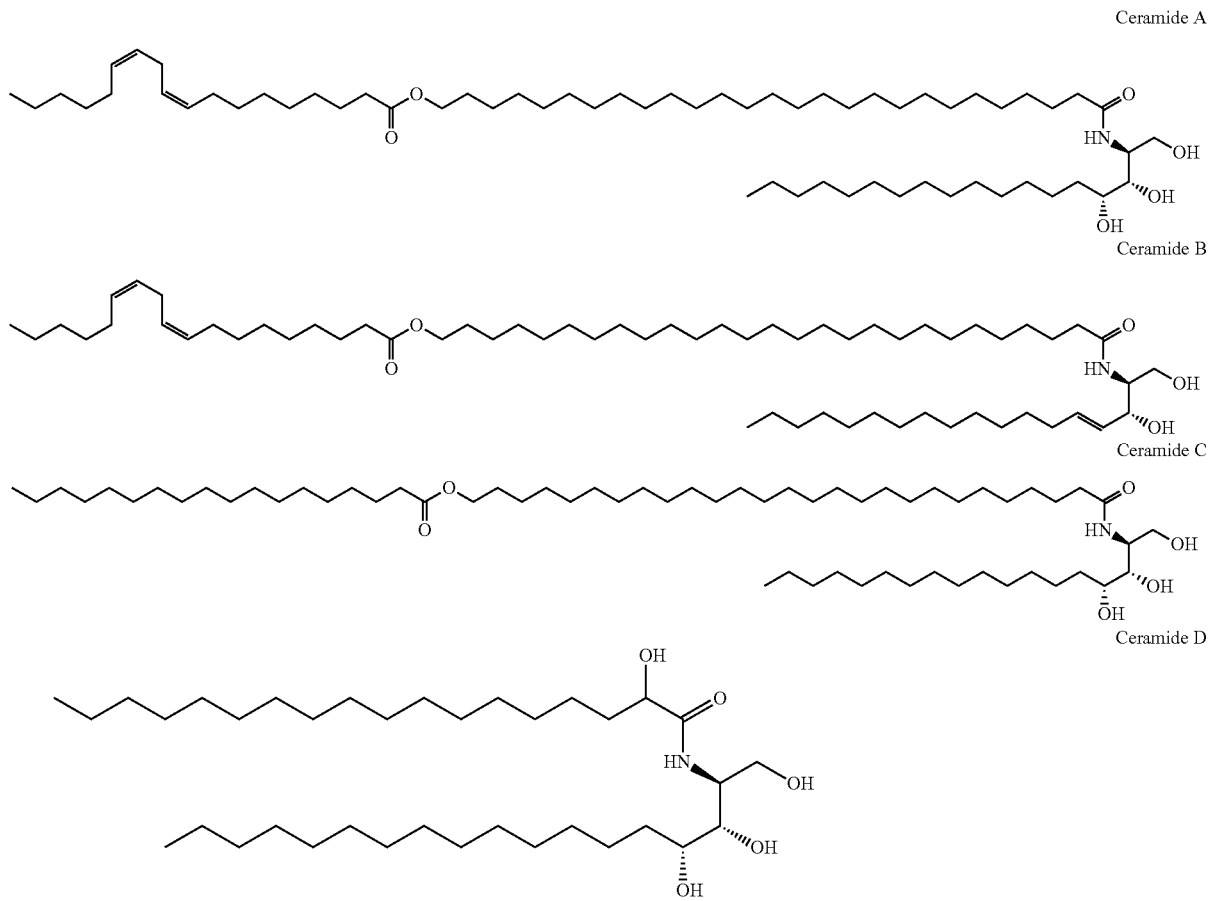

Evaluation

The obtained ceramide dispersion compositions were subjected to the following evaluations. The results are shown in Tables 1 to 3. In Table 2, the item "-" in the column regarding the evaluation means that the evaluation was not performed.

(1) Evaluation of Dispersion Stability

In order to evaluate dispersion stability of the ceramide dispersion composition, the particle diameters of dispersed particles in the ceramide dispersion compositions immediately after the preparation and after passage of time (after passage of 2 weeks, 50° C.) were measured. Regarding Comparative Example 9, because the ceramide dispersion composition was cloudy after passage of time, it was not possible to measure the particle diameter of dispersed particles after passage of time.

(1-1) Particle Diameter of Dispersed Particles in Ceramide Dispersion Composition Immediately after Preparation The particle diameter (volume average particle diameter) of dispersed particles in the ceramide dispersion composition immediately after the preparation was measured using a dynamic light scattering nanotrac particle size analyzer UPA (available from NIKKISO CO., LTD.). Measurement of volume average particle diameter was carried out in such determined as a volume average particle diameter (Mv) when the refractive index of the sample was set to 1.600, the refractive index of the dispersing medium was set to 1.333 (pure water), and the viscosity of the dispersing medium was set to the viscosity of pure water.

(1-2) Particle Diameter of Dispersed Particles in Ceramide Dispersion Composition after Passage of Time Forty-five milliliters of the ceramide dispersion composition were added in a 50 mL-volume glass vial container. After the container was tightly sealed and then kept in a constant-temperature bath at 50° C. for 2 weeks, the temperature was returned to 25° C. Subsequently, the particle diameter of dispersed particles was measured in the same manner as the ceramide dispersion composition immediately after preparation.

(2) Evaluation of Oxidation Stability

Tetrahydrofuran was added to 10 mg of the ceramide dispersion composition immediately after the preparation weighted in a 25 mL-volume volumetric flask so as to prepare a solution up to 25 mL. By analyzing the prepared solution using a high-performance liquid chromatography available from SHIMADZU CORPORATION, the content of ceramide was quantified. In addition, also as to the ceramide dispersion composition after passage of time obtained in the same manner as the above-mentioned evaluation of dispersion stability, the content of ceramide was quantified in the same manner as the ceramide dispersion composition immediately after the preparation. Furthermore, the residual rate (%) of ceramide after passage of time was calculated. Analyzing conditions under which the high-performance liquid chromatography was used are as follows.

—Analyzing Conditions—

Column: Inertsil SIL-100A (available from GL SCIENCES INC.), pore size of 3 μm

Eluate: hexane/isopropyl alcohol/methanol=25/70/5 (volume ratio)

Flow rate: 0.1 mL/min

Injection volume: 3 μL

Detection: electrospray ionization mass spectrometry (LCMS-2010EV, available from SHIMADZU CORPORATION)

(3) Evaluation of Barrier Film-Forming Ability

To the horny cell layer side of a cultured skin model (MatTek CORPORATION, EpiDerm EPI-200 (X)), 1% by mass solution of sodium dodecyl sulfate was applied. Fifteen minutes later, washing was performed with a phosphate buffer. Subsequently, water (control) or the ceramide dispersion composition was applied thereto, and then culture was carried out under a condition of 5 v/v % $CO_2$ at 37° C. for 2 days. The horny cell layer was peeled off by a trypsin treatment. The peeled horny cell layer was placed under 50% relative humidity environment at 22° C. for 24 hours, and then cut in a powder state. The powdered horny cell layer was placed into a capillary (inner diameter of 1 mm), and then subjected to a small-angle X-ray diffraction measurement (SPring-8 BL40B2 (STRUCTURAL BIOLOGY II BEAMLINE) or NanoSTAR instrument (BRUKER AXS GmBH, Germany)).

By deducting a background from a peak (primary diffraction) derived from a long periodic lamella structure (a structure in which layers each having a thickness of about 13 nm were layered), the area value was calculated as an index for a barrier film-forming ability.

TABLE 1

| | | EXAMPLE 1 | EXAMPLE 2 | EXAMPLE 3 | EXAMPLE 4 | EXAMPLE 5 | EXAMPLE 6 |
|---|---|---|---|---|---|---|---|
| FORMULATION (part) | CERAMIDE A | 0.3 | 0.3 | 0.3 | 0.3 | — | 0.3 |
| | CERAMIDE B | — | — | — | — | 0.3 | — |
| | CERAMIDE C | — | — | — | — | — | — |
| | CERAMIDE D | — | — | — | — | — | — |
| | TRISODIUM ASCORBYL PALMITATE PHOSPHATE | 0.5 | 1.0 | 2.0 | 0.5 | 1.0 | 0.1 |
| | ASCORBYL PALMITATE | — | — | — | — | — | — |
| | SODIUM ASCORBATE | — | — | — | — | — | — |
| | SODIUM ASCORBYL PHOSPHATE | — | — | — | — | — | — |
| | MAGNESIUM ASCORBYL PHOSPHATE | — | — | — | — | — | — |
| | TOCOPHEROL | — | — | — | — | — | — |
| | DECAGLYCEROL MONOMYRISTIC ACID ESTER | 4.0 | 4.0 | 4.0 | 4.0 | 4.0 | 4.0 |
| | LECITHIN | 4.0 | 4.0 | 4.0 | — | 4.0 | 4.0 |
| | CHOLESTEROL | 0.3 | 0.3 | 0.3 | 0.3 | 0.3 | 0.3 |
| | 1,3-BUTYLENE GLYCOL | 0.9 | 0.9 | 0.9 | 0.9 | 0.9 | 0.9 |
| | GLYCEROL | 35.0 | 35.0 | 35.0 | 35.0 | 35.0 | 35.0 |
| | IODOPROPYNYL BUTYL CARBAMATE | 0.015 | 0.015 | 0.015 | 0.015 | 0.015 | 0.015 |
| | ION EXCHANGED WATER | up to 100 | up to 100 | up to 100 | up to 100 | up to 100 | up to 100 |
| EVALUATION | PARTICLE DIAMETER OF DISPERSED PARTICLES JUST AFTER PREPARATION | 10 nm | 15 nm | 20 nm | 15 nm | 10 nm | 10 nm |
| | PARTICLE DIAMETER OF DISPERSED PARTICLES AFTER PASSAGE OF 2 WEEKS, 50° C. | 10 nm | 15 nm | 20 nm | 20 nm | 10 nm | 10 nm |
| | RESIDUAL RATE OF CERAMIDE AFTER PASSAGE OF 2 WEEKS, 50° C. | 95% | 95% | 95% | 95% | 95% | 92% |

TABLE 2

| | | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 | COMPARATIVE EXAMPLE 6 |
|---|---|---|---|---|---|---|---|
| FORMULATION (part) | CERAMIDE A | 0.3 | 0.3 | 0.3 | 0.3 | 0.3 | 0.3 |
| | CERAMIDE B | — | — | — | — | — | — |
| | CERAMIDE C | — | — | — | — | — | — |
| | CERAMIDE D | — | — | — | — | — | — |
| | TRISODIUM ASCORBYL PALMITATE PHOSPHATE | — | — | — | — | — | — |
| | ASCORBYL PALMITATE | — | 0.5 | — | — | — | — |
| | SODIUM ASCORBATE | — | — | 0.2 | 0.4 | — | — |
| | SODIUM ASCORBYL PHOSPHATE | — | — | — | — | 0.6 | 1.2 |
| | MAGNESIUM ASCORBYL PHOSPHATE | — | — | — | — | — | — |
| | TOCOPHEROL | — | — | — | — | — | — |
| | DECAGLYCEROL MONOMYRISTIC ACID ESTER | 4.0 | 4.0 | 4.0 | 4.0 | 4.0 | 4.0 |
| | LECITHIN | 4.0 | 4.0 | 4.0 | 4.0 | 4.0 | 4.0 |

TABLE 2-continued

|  |  |  |  |  |  |  |  |
|---|---|---|---|---|---|---|---|
|  | CHOLESTEROL | 0.3 | 0.3 | 0.3 | 0.3 | 0.3 | 0.3 |
|  | 1,3-BUTYLENE GLYCOL | 0.9 | 0.9 | 0.9 | 0.9 | 0.9 | 0.9 |
|  | GLYCEROL | 35.0 | 35.0 | 35.0 | 35.0 | 35.0 | 35.0 |
|  | IODOPROPYNYL BUTYL CARBAMATE | 0.015 | 0.015 | 0.015 | 0.015 | 0.015 | 0.015 |
|  | ION EXCHANGED WATER | up to 100 | up to 100 | up to 100 | up to 100 | up to 100 | up to 100 |
| EVALUATION | PARTICLE DIAMETER OF DISPERSED PARTICLES JUST AFTER PREPARATION | 10 nm | 10 nm | 20 nm | 20 nm | 20 nm | 40 nm |
|  | PARTICLE DIAMETER OF DISPERSED PARTICLES AFTER PASSAGE OF 2 WEEKS, 50° C. | 10 nm | 70 nm | 100 nm | 120 nm | 100 nm | 230 nm |
|  | RESIDUAL RATE OF CERAMIDE AFTER PASSAGE OF 2 WEEKS, 50° C. | 90% | 80% | — | — | — | — |

|  |  | COMPARATIVE EXAMPLE 7 | COMPARATIVE EXAMPLE 8 | COMPARATIVE EXAMPLE 9 | COMPARATIVE EXAMPLE 10 | COMPARATIVE EXAMPLE 11 |
|---|---|---|---|---|---|---|
| FORMULATION (part) | CERAMIDE A | 0.3 | 0.3 | 0.3 | 0.3 | 0.3 |
|  | CERAMIDE B | — | — | — | — | — |
|  | CERAMIDE C | — | — | — | — | — |
|  | CERAMIDE D | — | — | — | — | — |
|  | TRISODIUM ASCORBYL PALMITATE PHOSPHATE | — | — | — | — | — |
|  | ASCORBYL PALMITATE | — | — | — | — | — |
|  | SODIUM ASCORBATE | — | — | — | — | — |
|  | SODIUM ASCORBYL PHOSPHATE | — | — | — | — | — |
|  | MAGNESIUM ASCORBYL PHOSPHATE | 0.5 | 1.0 | 2.0 | — | — |
|  | TOCOPHEROL | — | — | — | 0.03 | 0.05 |
|  | DECAGLYCEROL MONOMYRISTIC ACID ESTER | 4.0 | 4.0 | 4.0 | 4.0 | 4.0 |
|  | LECITHIN | 4.0 | 4.0 | 4.0 | 4.0 | 4.0 |
|  | CHOLESTEROL | 0.3 | 0.3 | 0.3 | 0.3 | 0.3 |
|  | 1,3-BUTYLENE GLYCOL | 0.9 | 0.9 | 0.9 | 0.9 | 0.9 |
|  | GLYCEROL | 35.0 | 35.0 | 35.0 | 35.0 | 35.0 |
|  | IODOPROPYNYL BUTYL CARBAMATE | 0.015 | 0.015 | 0.015 | 0.015 | 0.015 |
|  | ION EXCHANGED WATER | up to 100 | up to 100 | up to 100 | up to 100 | up to 100 |
| EVALUATION | PARTICLE DIAMETER OF DISPERSED PARTICLES JUST AFTER PREPARATION | 30 nm | 30 nm | 30 nm | 10 nm | 10 nm |
|  | PARTICLE DIAMETER OF DISPERSED PARTICLES AFTER PASSAGE OF 2 WEEKS, 50° C. | 210 nm | 250 nm | (CLOUDY) | 10 nm | 20 nm |
|  | RESIDUAL RATE OF CERAMIDE AFTER PASSAGE OF 2 WEEKS, 50° C. | — | — | — | 80% | 80% |

TABLE 3

|  |  | EXAMPLE 2 | EXAMPLE 5 | REFERENCE EXAMPLE 1 | REFERENCE EXAMPLE 2 |
|---|---|---|---|---|---|
| FORMULATION (part) | CERAMIDE A | 0.3 | — | — | — |
|  | CERAMIDE B | — | 0.3 | — | — |
|  | CERAMIDE C | — | — | 0.3 | — |
|  | CERAMIDE D | — | — | — | 0.3 |
|  | TRISODIUM ASCORBYL PALMITATE PHOSPHATE | 1.0 | 1.0 | 1.0 | 1.0 |
|  | ASCORBYL PALMITATE | — | — | — | — |
|  | SODIUM ASCORBATE | — | — | — | — |
|  | SODIUM ASCORBYL PHOSPHATE | — | — | — | — |
|  | MAGNESIUM ASCORBYL PHOSPHATE | — | — | — | — |
|  | TOCOPHEROL | — | — | — | — |

TABLE 3-continued

| | | EXAMPLE 2 | EXAMPLE 5 | REFERENCE EXAMPLE 1 | REFERENCE EXAMPLE 2 |
|---|---|---|---|---|---|
| | DECAGLYCEROL MONOMYRISTIC ACID ESTER | 4.0 | 4.0 | 4.0 | 4.0 |
| | LECITHIN | 4.0 | 4.0 | 4.0 | 4.0 |
| | CHOLESTEROL | 0.3 | 0.3 | 0.3 | 0.3 |
| | 1,3-BUTYLENE GLYCOL | 0.9 | 0.9 | 0.9 | 0.9 |
| | GLYCEROL | 35.0 | 35.0 | 35.0 | 35.0 |
| | IODOPROPYNYL BUTYL CARBAMATE | 0.015 | 0.015 | 0.015 | 0.015 |
| | ION EXCHANGED WATER | up to 100 | up to 100 | up to 100 | up to 100 |
| EVALUATION | PARTICLE DIAMETER OF DISPERSED PARTICLES JUST AFTER PREPARATION | 15 nm | 10 nm | 20 nm | 20 nm |
| | PARTICLE DIAMETER OF DISPERSED PARTICLES AFTER PASSAGE OF 2 WEEKS, 50° C. | 15 nm | 10 nm | 20 nm | 20 nm |
| | RESIDUAL RATE OF CERAMIDE AFTER PASSAGE OF 2 WEEKS, 50° C. | 95% | 95% | 100% | 100% |
| | ABILITY TO FORM BARRIER FILM | 35 | 30 | 20 | 15 |

As is evident from Tables 1 and 2, the ceramide dispersion compositions of Examples 1 to 6, each of which contained ceramide A or ceramide B, having an unsaturated double bond in the O-acyl moiety, together with a surfactant and trisodium ascorbyl palmitate phosphate, had extremely small particle diameters of dispersed particles immediately after the preparation of from 10 μm to 20 μm, and had almost no change in particle diameters of dispersed particles after passage of time. As such, the dispersion stability was excellent. In addition, the ceramide dispersion compositions of Examples 1 to 6 had higher residual rates of ceramide after passage of time than that of the ceramide dispersion composition of Comparative Example 1 in which trisodium ascorbyl palmitate phosphate was not used. As such, the oxidation stability was excellent.

In contrast, the ceramide dispersion compositions of Comparative Examples 2 to 9 in which ascorbyl palmitate, sodium ascorbate, sodium ascorbyl phosphate, or magnesium ascorbyl phosphate was used instead of trisodium ascorbyl palmitate phosphate had remarkably lower dispersion stability than that of the ceramide dispersion composition of Comparative Example 1.

In addition, the ceramide dispersion compositions of Comparative Examples 10 and 11 in which tocopherol was used instead of trisodium ascorbyl palmitate phosphate had lower oxidation stability than that of the ceramide dispersion composition of Comparative Example 1.

As is evident from Table 3, the ceramide dispersion compositions of Examples 2 and 5 which contained ceramide A or ceramide B having an unsaturated double bond in the O-acyl moiety had higher barrier-film forming ability in the case of being applied to the skin than those of the ceramide dispersion composition of Reference Example 1 which contained ceramide C having no unsaturated double bond in the O-acyl moiety and the ceramide dispersion composition of Reference Example 2 which contained ceramide D not having an O-acyl moiety.

What is claimed is:
1. A ceramide dispersion composition, comprising:
at least one ceramide represented by Formula (1) or Formula (2);
a surfactant; and
trisodium ascorbyl palmitate phosphate:

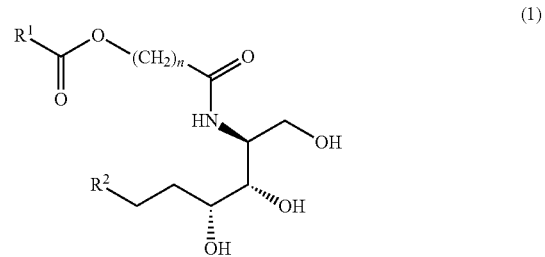

(1)

wherein, in Formula (1), $R^1$ represents an aliphatic hydrocarbon group having at least one unsaturated double bond, $R^2$ represents an alkyl group having 9 or more carbon atoms, and n represents an integer from 20 to 34; and

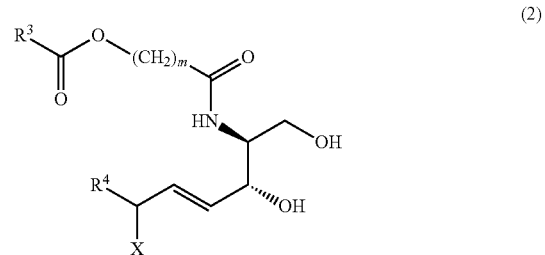

(2)

in Formula (2), $R^3$ represents an aliphatic hydrocarbon group having at least one unsaturated double bond, $R^4$ represents an alkyl group having 9 or more carbon atoms, m represents an integer from 20 to 34, and X represents a hydrogen atom or a hydroxyl group.

2. The ceramide dispersion composition according to claim 1, wherein the aliphatic hydrocarbon group having at least one unsaturated double bond represented by $R^1$ or $R^3$ has 15 or more carbon atoms.

3. The ceramide dispersion composition according to claim 1, wherein the aliphatic hydrocarbon group having at least one unsaturated double bond represented by $R^1$ or $R^3$ has from 1 to 3 double bonds.

4. The ceramide dispersion composition according to claim 1, wherein the surfactant comprises a nonionic surfactant.

5. The ceramide dispersion composition according to claim 1, further comprising lecithin.

6. The ceramide dispersion composition according to claim 1, further comprising cholesterol.

7. The ceramide dispersion composition according to claim 1, wherein a content of trisodium ascorbyl palmitate phosphate with respect to a content of the at least one ceramide represented by Formula (1) or Formula (2) is from 1 time by mass to 8 times by mass.

8. The ceramide dispersion composition according to claim 1, wherein a content of the surfactant with respect to a content of the at least one ceramide represented by Formula (1) or (2) is from 1 time by mass to 70 times by mass.

9. The ceramide dispersion composition according to claim 1, which is an external agent for skin.

\* \* \* \* \*